United States Patent [19]

Cameron et al.

[11] 4,394,444

[45] Jul. 19, 1983

[54] COFACTOR INDICATOR COMPOSITIONS

[75] Inventors: Erma C. Cameron, Mishawaka; Claude R. Gunter, Elkhart; Rodric H. White-Stevens, Howe, all of Ind.

[73] Assignee: Miles Laboratories, Inc., Elkhart, Ind.

[21] Appl. No.: 390,252

[22] Filed: Jun. 21, 1982

[51] Int. Cl.³ ............................................. C12Q 1/60
[52] U.S. Cl. ........................................ 435/11; 435/14; 435/15; 435/26; 435/28; 435/805; 435/810
[58] Field of Search ................... 252/408 R; 424/2, 7; 435/4, 11, 14, 18, 20, 25, 26, 28, 805, 810, 15; 436/34, 904

[56] References Cited

U.S. PATENT DOCUMENTS

| | | | |
|---|---|---|---|
| 3,384,555 | 5/1968 | Guilbault | 435/25 |
| 3,703,591 | 11/1972 | Bucolo | 435/25 |
| 3,886,045 | 5/1975 | Meiattini | 435/14 |
| 3,964,974 | 6/1976 | Banauch et al. | 435/14 |
| 3,975,398 | 8/1976 | Werner et al. | 435/14 |
| 4,101,381 | 7/1978 | Klose et al. | 435/11 |
| 4,119,405 | 10/1978 | Lan | 435/3 |
| 4,120,755 | 10/1978 | Pierre et al. | 435/14 |
| 4,131,430 | 12/1978 | Denney | 436/108 |

OTHER PUBLICATIONS

Storm et al., "The Effect of Variation of Cofactor & Substrate Structure on the Action of Phenylalanine Hydroylase", *Biochem. & Biophys. Res. Comm.*, Jul. 1968, pp. 788-793.
White-Stevens et al., "Studies of a Flavoprotein, Salicylate Hydroxylase," *J. Biol. Chem.*, Apr. 1972, pp. 2358-2370.
Howell et al., "Purification & Properties of p-Hydroxybenzoate Hydroxylase from Pseudomonas Fluorescens," *J. Biol Chem.*, Jul. 1972, pp. 4340-4350.
Spector et al., "Studies on the Effector Specificity of p-Hydroxybenzoate Hydroylase from Pseudomonas Fluorescens," *J. Biol Chem.*, Jul. 1972, pp. 4679-4687.
Howell et al., "A Non-Substrate Effector of p-Hydroxybenzoate Hydroxylase," *Biochem. & Biophys Comm.*, Jul. 1970, pp. 887-893.

*Primary Examiner*—Peter A. Hruskoci
*Attorney, Agent, or Firm*—Roger N. Coe

[57] ABSTRACT

A composition, test device, method of making a test device and process for determination of an analyte in a liquid sample are disclosed. More particularly, there is provided a composition for the determination of an analyte in a sample which composition comprises an analyte-responsive component comprising a pyridine nucleotide susceptible of reduction in response to the presence of said analyte and at least one constituent interreactive with said analyte to cause reduction of the pyridine nucleotide, an uncoupler effective to generate an oxidizing substance from the reduced form of said pyridine nucleotide, a peroxidatively active substance, and an indicator which, when oxidized, is not susceptible to reduction by said reduced pyridine nucleotide. The pyridine nucleotide can be nicotine adenine dinucleotide (NAD) or nicotine adenine dinucleotide phosphate (NADP).

36 Claims, No Drawings

COFACTOR INDICATOR COMPOSITIONS

This application is a continuation of application Ser. No. 83,408, filed Oct. 10, 1979 now abandoned.

BACKGROUND OF THE INVENTION

1. Field of the Invention

The present invention relates generally to the field of diagnostic tests and, more particularly, to those tests useful in qualitative and quantitative determination of biological components, such as lactic acid and ketone bodies, in which tests such components are converted to an oxidizing substance, such as a peroxide.

2. Description of the Prior Art

The technique of using a tetrazolium compound and an electron-carrying intermediary (such as phenazine methosulfate or diaphorase) to turn reduced nicotine adenine dinucleotide (phosphate) [NAD(P)H] into color has been known for some time. Markert, C. L. and Moller, F., Proc. Nat. Acad. Sci. U.S. 45, 753 (1959); Tsao, M. U., Arch. Biochem. Biophys., 90, 234 (1960); Dewey, M. M. and Conklin, J. L.,Proc. Soc. Exp. Biol. and Med. 105, 492 (1960); Nachlas, M. M., Margulies, S. I., Goldberg, J. D., and Seligman, A. M., Anal. Biochem. 1, 317 (1960); Babson, A. L. and Phillips, G. E., Clin. Chim. Acta 12, 210 (1965); Gay, R. J., McComb, R. B., and Bowers, G. N., Clin. Chem. 14, 740 (1968). However, this technique suffers from the problems of phenazine methosulfate light sensitivity, insolubility of the formazan dye product, and diaphorase insolubility and instability.

The reaction of NAD(P)H with copper sulfate yields a cuprous ion that can then form a chelation product into neocuproin. This chelation product is colored. Morgenstern, S., Flor, R., Kessler, G., and Klein, B., Anal. Biochem 13, 149 (1965).

Reduced nicotine adenine dinucleotide (NADH) reacts with 2-oxobutyrate and 2,4-dinitrophenylhydrazine in the presence of lactate dehydrogenase to form 2,4-dinitrophenylhydrazone. King, J., Practical Clinical Enzymology, D. Van Nostrand Co., Ltd., p. 55, (1965); Cabaud, P. G. and Wroblewski, F., Am. J. Clin. Path. 30, 234 (1958). This product is colored. However, this reaction requires two separate discrete steps for color generation. Moreover, the accuracy of the method has been questioned. Massod, M. F., Franey, R. J., Therrien, M. E., Rideout, P. T., and Babcock, M. T., Am. J. Clin. Path. 42, 623 (1964).

Evidence for the existence of an uncoupling hydroxylase was first found in 1961 by Kaufman. Kaufman, S., Biochim. Biophys. Acta 51, 619 (1961). The nonstoichiometric nature of the hydroxylase reaction indicated that some product, other than hydroxylated substrate, was being produced. Since that time many other examples of this phenomenon have been seen. Most uncoupling hydroxylases are not completely uncoupled. In other words, there is some hydroxylated product formed and some hydrogen peroxide formed. A few can be completely uncoupled by certain pseudosubstrates. In other words, there is no hydroxylated product formed. An example of a 100% uncoupled system is salicylate hydroxylase and benzoate. White-Stevens, R. H. and Kamin, H., J. Biol. Chem. 247, 2358 (1972); White-Stevens, R. H., Kamin, H. and Gibson, Q. H., J. Biol. Chem. 247, 2371 (1972); White-Stevens, R. H., Kamin, H., and Gibson, Q. H. in "Oxidation Reduction Enzymes", Akeson, A. and Ehrenberg, A., eds., p. 453, Pergamon Press, Oxford and New York (1972); White-Stevens, R. H. and Kamin, H. Biochem. and Biophys. Res. Comm. 38, 882 (1970). Other examples of completely or partially uncoupled hydroxylases include phenylalanine hydroxylase, Storm, C. B., and Kaufman, S., Biochem and Biophys. Res. Comm. 32, 788 (1968); Fisher, D. B. and Kaufman, S., J. Biol. Chem. 248, 4300 (1973); p-hydroxybenzoate hydroxylase, Spector, T. and Massey, V., J. Biol. Chem. 247, 4679 (1972); Howell, L. G., Spector, T., and Massey, V., J. Biol. Chem., 247, 4340 (1972); Howell, L. G. and Massey, V., Biochem. and Biophys. Res. Comm. 40, 887 (1970); and orcinol hydroxylase, Ohta, Y., Higgins, I. J., and Ribbons, D. W., J. Biol. Chem. 250, 3814 (1975).

There has been only one publication in which the hydroxylase system has been linked to peroxidase. This was done for the purpose of detecting hydrogen peroxide formation rather than for the assay of any component taking part in the reactions. Storm, C. B., and Kaufman, S., supra. Peroxidase was used to oxidize a reduced cofactor that was part of the hydroxylase reaction. The altered ratio of hydroxylated product formed indicated that hydrogen peroxide had been present. This reaction did not involve the formation of a colored product. The object of the experiment was to demonstrate that the hydroxylase reaction had generated some $H_2O_2$. No reference has been found that discloses the use of uncoupling hydroxylases, either alone or in combination with a peroxidase system, as an assay or a detection method.

SUMMARY OF THE INVENTION

The composition of the invention for generating color from a reduced pyridine nucleotide does not suffer from problems that plaque the prior art methods. For instance, one of the most common methods of generating color from NAD(P)H is the use of a tetrazolium salt and intermediate electron carrier, such as phenazine methosulfate or diaphorase. However, the phenazine methosulfate is very light sensitive, the reduced dye product is insoluble, and diaphorase is difficultly soluble. These are all problems which are overcome by the present invention. Furthermore, the composition according to the invention is very versatile. There is a choice among indicator systems, among uncoupling hydroxylases, and among methods to generate a reduced pyridine nucleotide. This versatility includes a choice of assaying for an analyte in a sample as well as assaying for any predetermined component of the composition.

The overall scheme for NAD(P) is as follows:

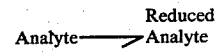

Analyte ⟶ Reduced Analyte

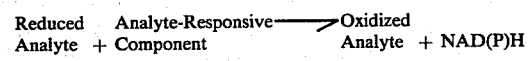

Reduced Analyte + Analyte-Responsive Component ⟶ Oxidized Analyte + NAD(P)H

Equation II

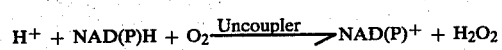

$H^+ + NAD(P)H + O_2 \xrightarrow{\text{Uncoupler}} NAD(P)^+ + H_2O_2$

Equation III

-continued

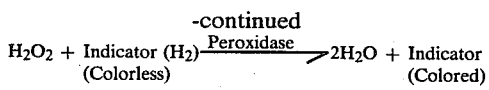

Thus, all these advantages are provided in a composition for the determination of an analyte in a sample which composition comprises an analyte-responsive component comprising a pyridine nucleotide susceptible of reduction in response to the presence of said analyte and at least one constituent interreactive with said analyte to cause reduction of the pyridine nucleotide, an uncoupler effective to generate an oxidizing substance from the reduced form of said pyridine nucleotide, a peroxidatively active substance, and an indicator which, when oxidized, is not susceptible to reduction by said reduced pyridine nucleotide. The pyridine nucleotide can be nicotine adenine dinucleotide (NAD) or nicotine adenine dinucleotide phosphate (NADP).

DESCRIPTION OF THE PREFERRED EMBODIMENTS

Although specific terms are used for clarity, these terms refer only to the embodiments selected for illustration, and are not intended to limit the scope of the invention.

The invention is a means of generating visible color, either in solution or device format, from reduced pyridine nucleotides. The analyte-responsive component includes a pyridine nucleotide susceptible of reduction in response to the presence of an analyte and at least one constituent interreactive with said analyte to cause reduction of the pyridine nucleotide (Equation I). The pyridine nucleotide is either initially present in its reduced form or is reduced by the action of at least one constituent interreactive with the analyte to reduce the pyridine nucleotide; for example an enzyme, which requires the pyridine nucleotide as a cofactor, and its substrate. If the reduced pyridine nucleotide is the analyte in question no interreactive constituent is necessary and the reaction proceeds from Equation II. This reduced pyridine nucleotide then is made to generate an oxidizing substance such as $H_2O_2$ by action of an uncoupler, such as an uncoupling hydroxylase and a pseudosubstrate therefor (Equation II). In the presence of a peroxidatively active substance, such as a peroxidase, the peroxide thus formed causes the indicator to generate a color (Equation III). All substances necessary for this reaction, except the analyte, are compatible in solution or on a carrier to form a device.

Equation I

Any enzymatic reaction constituent that can generate, or that can be coupled to another enzymatic system to generate, reduced pyridine nucleotide can be used as the interreactive constituent in the analyte-responsive component. Therefore, either the substrate of these enzymes or the enzymes themselves can be detected or assayed as the analyte of this system.

In a first embodiment the interreactive constituent of the analyte-responsive component can be an analyte-specific enzyme when the analyte is the substrate of that enzyme, and is an analyte-specific substrate when the analyte is an enzyme specific for that substrate. In a preferred embodiment the enzyme is a dehydrogenase. Exemplary substrate/enzyme pairs include lactate/lactate dehydrogenase, β-hydroxybutyrate/β-hydroxybutyrate dehydrogenase, α-hydroxybutyrate/α-hydroxybutyrate dehydrogenase, alcohol (such as ethanol)/alcohol dehydrogenase, a steroid (such as cholesterol)/steroid dehydrogenase and glucose/glucose dehydrogenase. In another preferred embodiment, the substrate/enzyme pair is 6-hydroxy nicotinate/p-hydroxybenzoate hydroxylase.

In another embodiment at least one interreactive constituent of the analyte-responsive component is an analyte-specific enzyme and an enzyme interreactive with the product of the reaction of said analyte-specific enzyme with the analyte to reduce the pyridine nucleotide. In one example of this embodiment said analyte-specific enzyme is a lipase and said enzyme interreactive with the product of the reaction of said lipase with the analyte to reduce the pyridine nucleotide is glycerol dehydrogenase. In another example of this embodiment said analyte-specific enzyme is hexokinase and said enzyme interreactive with the product of the reaction of said hexokinase with the analyte to reduce the pyridine nucleotide is glucose-6-phosphate dehydrogenase.

In the inverse of this embodiment said at least one interreactive constituent is an analyte-specific substrate and an enzyme interreactive with the product of the reaction of said analyte-specific substrate with the analyte to reduce the pyridine nucleotide (i.e., the substrate-specific enzyme and the substrate are conjugate pairs, therefore either may be designated as the analyte). By way of example, said analyte-responsive substrate is a triglyceride, the analyte now being lipase, and said enzyme interreactive with the product of the reaction of said triglyceride with the analyte to reduce the pyridine nucleotide is glycerol dehydrogenase.

The reaction sequences of these examples of a test for a dehydrogenase or its substrate are as follows:

GENERAL FORM:

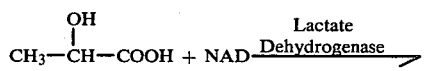

Oxidized Substrate + NAD(P)H, where the analyte is either the substrate or the substrate-specific enzyme and the interreactive constituent of the analyte-responsive component is the conjugate of the enzyme/substrate pair.

SPECIFIC EXAMPLES

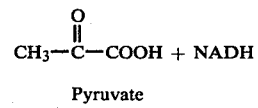

$$CH_3-C-COOH + NADH$$

Pyruvate

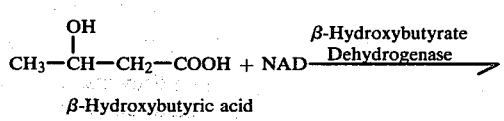

β-Hydroxybutyric acid

-continued

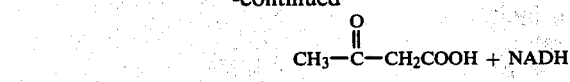

Acetoacetic Acid

C.

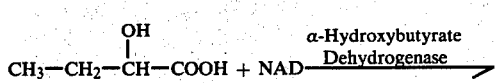

α-Hydroxybutyric acid

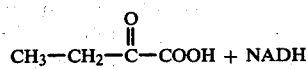

α-Oxobutyrate

D.

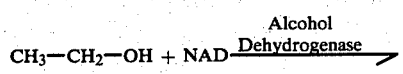

Ethanol

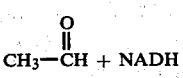

Acetaldehyde

E.

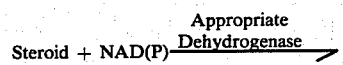

Oxidized Steroid + NAD(P)H

F.

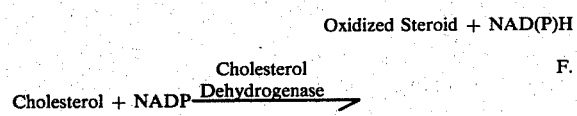

Cholestenone + NADPH

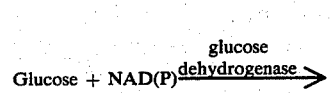

Glucono - δ - Lactone + NAD(P)H

2.

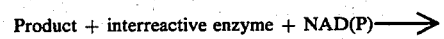

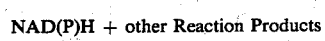

where the interreactive constituent comprises the analyte-specific enzyme and an enzyme interreactive with the product of the reaction of said analyte specific enzyme with the second enzyme to reduce the pyridine nucleotide a.

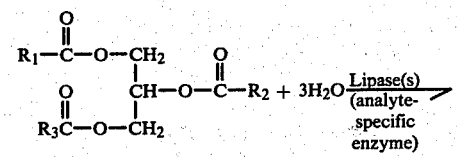

Triglyceride (analyte)

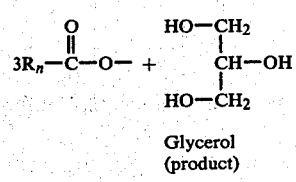

Glycerol (product)

wherein $R_1$, $R_2$ and $R_3$ are independently selected from the group of fatty acids. $R_n$ connotes any of $R_1$, $R_2$ or $R_3$.

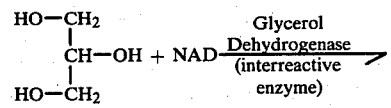

Glycerol (product)

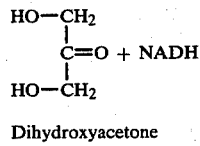

Dihydroxyacetone b.

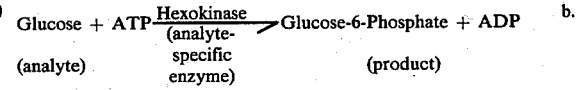

(product)

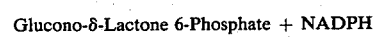

Glucono-δ-Lactone 6-Phosphate + NADPH

Equations II and III

The uncoupling hydroxylase reaction which occurs in response to the presence of the reduced pyridine nucleotide is as follows:

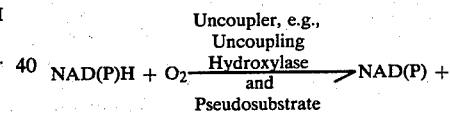

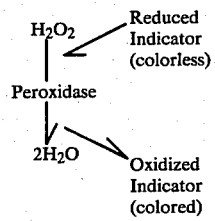

Studies of these two reactions revealed that components of the uncoupling hydroxylase reaction (II) were interfering with the peroxidase reaction (III), but that the reverse was not true. The NADH supplied for the salicylate hydroxylase reaction was acting as a reducing agent to reduce, and thereby bleach, oxidised o-tolidine indicator (colored) as fast as it was formed. A search was made for reduced indicator systems for the peroxidase reaction which, when oxidized by peroxidase, were not susceptible to reduction by NADH. Several nonreversible indicators were found to be insensitive to reduction by NADH.

The following coupled irreversible indicator has been used, by way of example, for color generation:

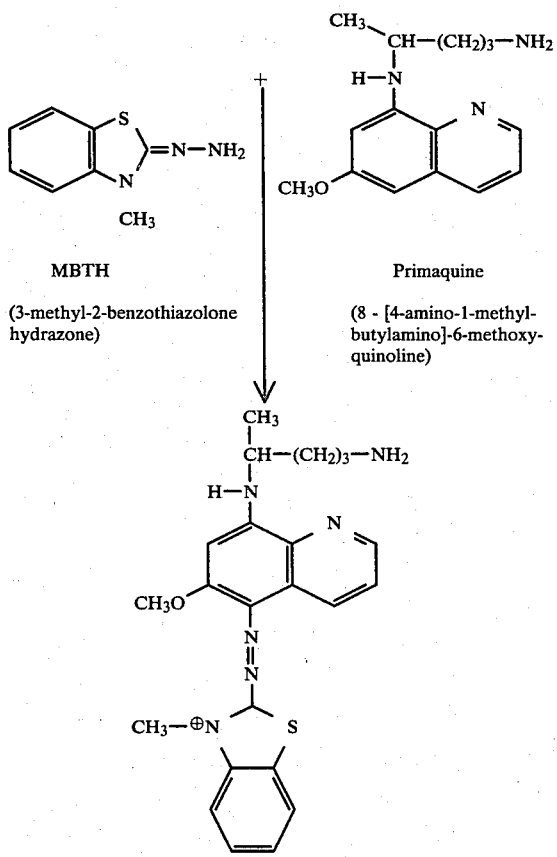

MBTH
(3-methyl-2-benzothiazolone hydrazone)

Primaquine
(8 - [4-amino-1-methyl-butylamino]-6-methoxy-quinoline)

Other such hydrazone/coupler redox indicators are suitable for use with the invention and are described, inter alia, in U.S. Pat. No. 4,119,405. A single coupler may be selected or more than one coupler can be used in combination.

The composition can be used as a solution for determination of the analyte. The solvents used in preparing the solutions can be water, physiological solutions or others known for their suitability. The composition is preferably used to detect the analyte by adding it to a specimen such as urine, cerebrospinal fluid, tissue culture supernatant serum, plasma or whole blood.

When the composition is used in solution form, the pyridine nucleotide is preferably used in concentrations of from about 0.1 mM (millimolar) to about 10 mM. The preferred range is from about 1 mM to about 10 mM. When a dehydrogenase is part of the analyte-responsive component, concentrations thereof are preferably from about 0.0003 milligrams per milliliter (mg/ml) to about 0.1 mg/ml. When lipase is part of the analyte responsive component, concentrations thereof are preferably from about 0.0001 mg/ml to about 0.1 mg/ml. When hexokinase is part of the analyte responsive component, concentrations thereof are preferably from about 0.0005 mg/ml to about 0.2 mg/ml. The uncoupling hydroxylase is present in concentrations of from about 0.001 mg/ml to about 0.01 mg/ml and its pseudosubstrate is present in concentrations of from about 0.5 mM to about 30 mM. When peroxidase is present, concentrations thereof are preferably from about T0.001 mg/ml to about 0.1 mg/ml. The indicator is preferably used in concentrations of from about $10^{-5}$ Molar (M) to about $10^{-3}$ M. The enzymes and other reagents in the examples can be obtained from, inter alia, Research Products Division, Miles Laboratories, Inc., Elkhart, Indiana. The hydroxylases were prepared as described in the literature.

Also provided are test devices incorporating the test composition of the invention and a method of making such test devices which comprises incorporating a carrier with the composition. In addition to impregnation, incorporation of the carrier with the composition can be effected by other suitable techniques, such as by printing or spraying the test composition onto the carrier.

The term carrier refers to matrices which are insoluble in and maintain their structural integrity when exposed to physiological or other liquid to be tested. Suitable matrices which may be used include paper, cellulose, wood, synthetic resin fleeces, glass fiber, nonwoven and woven fabrics, various organic polymers, such as polypropylene, and other organic materials well known as film formers to those skilled in the art. Alternatively, the carrier may take the form of a pressed or molded tablet containing conventional carrier material. For convenience, the carrier can be suitably attached to an insoluble support or handle member which can be made from polystyrene.

The test device is prepared by a process which comprises incorporating a carrier with a composition according to the invention. Where the composition is in liquid form this is followed by drying. The device is preferably prepared by a single impregnation process. The concentrations of reagents used in the impregnation solution range from about 0.1 mM up to a saturated solution. Most generally useful for the pyridine nucleotide is a concentration of about 50 mM. Peroxidase concentration is from about 0.015 mg/ml to about 2 mg/ml in the impregnation solution. The solvents used in preparing the impregnation solutions can be water, physiological solutions, organic solvents or combinations thereof.

The test device is advantageously used by momentarily dipping it in a test sample or by otherwise introducing a test sample into the carrier matrix, whereby a detectable color change results when the analyte is present. The volumetric capacity of the carrier serves to limit the amount of sample absorbed thereby and to which the test composition incorporated therewith is exposed. Any excess sample can be removed by washing or blotting the carrier to thereby limit the amount of sample tested to the volume thereof which has actually entered the carrier matrix. The test device can be used in the same way when samples of plasma, serum or other body fluids are tested.

Test devices in the form of treated carrier matrices are often stored for considerable periods of time before use, and it is therefore desirable that the reagents chosen are not easily auto-oxidizable in air. Advisably, the test devices should be protected from exposure to light and in some cases it is desirable to keep them sealed in a moisture repellent package which is opened only for removal of one or more test devices shortly before use.

Reflectance readings of color produced by reaction with the analyte present in sample can be obtained from commercially available spectrophotometers such as Beckman DK-2 Spectrophotometer, Beckman Instruments, Inc., Fullerton, California or Spectrocolorimeter SCF-1, Israel Electro-Optical Industry Ltd. (distributed in the U.S. by Broomer Research Corporation, Plainwell, Long Island, N.Y.).

Examples II and III illustrate preferred embodiments of the invention.

EXAMPLE I

This example reports tests performed on four compositions, each of which included a different indicator. The four different indicators tested were (1) o-tolidine, (2) MBTH+N,N-dimethylaniline, (3) MBTH+chromotropic acid, and (4) MBTH+primaquine.

Compositions were prepared, in solution format, to have concentrations of species (except o-tolidine test) as follows: 0.31 M citrate (pH 7.59), 0.03 M sodium benzoate, 1 mM EDTA, 147 µM NADH, 0.005 mg/ml horseradish peroxidase, and 100 µM each of MBTH and its coupler. For the o-tolidine test, 127.5 µM of o-tolidine was used and 0.02 M potassium phosphate (pH 7.6) was substituted for the citrate buffer. All other species were the same as for the three compositions containing MBTH+coupler. The reaction was permitted to proceed by introduction of salicylate hydroxylase to a concentration of 1.17 µg/ml. These reactions were carried out under ambient laboratory conditions and the rate of color development was observed on a Gilford 2000 spectrophotometer. The wavelengths at which color development was read for each indicator was that determined to be optimal for the particular species.

The results obtained from observing the above reactions were as follows:

| Reduced Indicator | Rate of Color Development | |
|---|---|---|
| | Wavelength | ΔOD/min. |
| o-tolidine | 411 | 0.0000 |
| MBTH + N,N—dimethylaniline | 585 | 0.0112 |
| MBTH + Chromotropic acid | 565 | 0.186 |
| MBTH + primaquine | 510 | 0.266 |

The results reported above show that compositions which include MBTH+primaquine as indicator will yield color development from NADH but that compositions including o-tolidine would not.

EXAMPLE II

LACTIC ACID ASSAY

Diabetic patients are at increased risk of developing lactic acidosis; this situation may be aggravated by the hypoglycemic drug phenformin. Therefore, there is a need for a lactic acid test.

In this example lactate was converted according to the invention into color in solution and device format using composition formulations as follows:

| Reagent | Solution Test | Device Impregnation Solutions |
|---|---|---|
| First Dip | | |
| pyrophosphate buffer pH 8.0 | 0.05M | 0.05M |
| EDTA | 1.0 mM | 1.0 mM |
| Sodium Benzoate | 30 mM | 30 mM |
| NAD | 5.25 mM | 52.5 mM |
| peroxidase | .055 mg/ml | .5 mg/ml |
| polyvinyl pyrrolidone | — | 6.4 mg/ml |
| salicylate hydroxylase | .0117 mg/ml | 1.17 mg/ml |
| lactate dehydrogenase | .0017 mg/ml | 0.017 mg/ml |
| Second Dip | | |
| MBTH.HCl | 0.1 mM | 10 mM |
| primaquine diphosphate (PDP) | 0.1 mM | 10 mM |
| benzene | solvent | solvent |

In solution, the entire system is present in a single cuvette and the progress of the reaction, produced by introduction of aqueous lactate solutions having the concentrations shown below, was followed by observing the increase in absorbance at 510 nanometers (nm) in a spectrophotometer.

To form devices, separate sheets of Eaton-Dikeman 205 filter paper (Eaton-Dikeman, Mount Holly Springs, PA. 17065) were impregnated to saturation, each with the impregnation solutions identified above. After each impregnation the sheets were subjected to 60° C. in a standard laboratory oven until dry. These paper sheets, containing the dried residue of the impregnation solutions, were then cut to 2.5 millimeter (mm) by 2.5 mm squares. The devices were then backed by double-faced adhesive tape and fixed thereby to plastic support members. To start color development, aqueous lactate solutions having the concentrations shown below were pipetted onto the devices. The color development is followed by eye, or in a reflectance spectrophotometer.

Both in solution and with devices, levels of lactate encompassing the physiological range of lactate in blood (i.e., 0.6 to 6 mM) were assayed. In solution, the levels were distinguished from each other by the rate of color development. The rate of color development is reported as the change in optical density per minute (ΔOD/min). The more lactate present, the more rapid is color development. When devices were used in testing, the levels were distinguished by the percentage of reflectance observed at one minute. The more lactate, the more color formed at one minute.

With these solution and device conditions, the response to lactate was as follows:

| Lactate Concentration | |
|---|---|
| Solution | |
| | Rate of color development (ΔOD/min at 510 nm) |
| 7.75 mM | .576 |
| 2.58 mM | .395 |
| 0.65 mM | .148 |
| 0 | .0116 |
| Device | |
| | % reflectance at 1 minute at 520 nm |
| 77.5 mM | 19.2% |
| 7.75 mM | 29.1% |
| 0.775 mM | 40.2% |
| 0 | 54.9% |

The results reported for tests performed both in solution and with devices show that the composition according to the invention is effective in quantitative detection of lactic acid in either format.

EXAMPLE III

ASSAY FOR KETONE BODIES

β-Hydroxybutyric acid accounts for approximately 80% of the total ketone bodies found in urine. Presently available tests to detect ketone bodies in urine assay only acetoacetic acid, which accounts for only about 20% of the ketone bodies. Therefore, a test for β-hydroxybutyric acid would be a useful ketone body test.

β-hydroxybutyric acid was converted into color according to the invention both in solution and device format. The reagent concentration in solution tests and in devices, prepared as in Example II, are as stated for the lactate assay of Example II, with the following changes:

| Reagent | Solution Test | Device Impregnation Solutions |
|---|---|---|
| NAD | 3.5 mM | 52.5 mM |
| β-hydroxybutyrate dehydrogenase | .0017 mg/ml | .2 mg/ml |
| lactate dehydrogenase | omitted | omitted |
| polyvinyl pyrrolidone | omitted | omitted |

In solution, the entire system is present in a single cuvette and the progress of the reaction, produced by introduction of aqueous β-hydroxybutyric acid solutions having the concentrations shown below, is followed by observing the increase in absorbance at 510 nm in a spectrophotometer. The devices were prepared as in Example II with the changes in formulation noted above. The β-hydroxybutyric acid solutions were introduced and the color development was followed by eye, and in a reflectance spectrophotometer.

Both in solution and with devices, levels of β-hydroxybutyric acid encompassing levels found in urine were assayed. In solution the levels were distinguished from each other by the rate of color development. When devices were used in testing, the levels were distinguished by the percentage of reflectance observed at one minute.

With these solution and device conditions, the response to β-hydroxybutyric acid was as follows:

| β-Hydroxybutyric acid Concentration | Solution Rate of color development (ΔOD/min at 510 nM) |
|---|---|
| 2.5 mM | .152 |
| 5.0 | .187 |
| 10.0 | .201 |
| 30.0 | .229 |

| | Device % reflectance at 1 min. at 520 nm |
|---|---|
| 0 | 50.8% |
| 2.5 mM | 34.6% |
| 10.0 | 25.6% |
| 30.0 | 20.9% |

The results obtained in this experiment demonstrate that the composition according to the invention is effective in quantitative detection of β-hydroxybutyric acid in solution and device formats.

Although the invention has been described with a certain degree of particularity, numerous changes may be resorted to without departing from the scope of the invention.

What is claimed is:

1. A composition for the determination of an analyte in a sample which composition comprises:
   an analyte-responsive component comprising a pyridine nucleotide susceptible of reduction in response to the presence of said analyte and at least one constituent interreactive with said analyte to cause reduction of the pyridine nucleotide;
   a hydroxylase capable of being uncoupled and a pseudosubstrate capable of uncoupling said hydroxylase, which hydroxylase and pseudosubstrate, in the presence of the reduced form of said pyridine nucleotide, are effective to generate hydrogen peroxide;
   a peroxidatively active substance; and
   a hydrazone indicator comprising a hydrazone and a coupler, which indicator, when in its oxidized form, cannot be reduced by said pyridine nucleotide.

2. The composition of claim 1 wherein said pyridine nucleotide is nicotine adenine dinucleotide.

3. The composition of claim 1 wherein said pyridine nucleotide is nicotine adenine dinucleotide phosphate.

4. The composition of claim 1 wherein said at least one interreactive constitutent is an analyte-specific enzyme.

5. The composition of claim 4 wherein said enzyme is a dehydrogenase.

6. The composition of claim 5 wherein said enzyme is lactate dehydrogenase.

7. The composition of claim 5 wherein said enzyme is β-hydroxybutyrate dehydrogenase.

8. The composition of claim 5 wherein said enzyme is α-hydroxybutyrate dehydrogenase.

9. The composition of claim 5 wherein said enzyme is alcohol dehydrogenase.

10. The composition of claim 5 wherein said enzyme is a steroid dehydrogenase.

11. The composition of claim 10 wherein said enzyme is cholesterol dehydrogenase.

12. The composition of claim 5 wherein said enzyme is glucose dehydrogenase.

13. The composition of claim 1 wherein said at least one interreactive constituent is an analyte-specific enzyme and an enzyme interreactive with the product of the reaction of said analyte-specific enzyme with the analyte.

14. The composition of claim 13 wherein said analyte-responsive enzyme is a lipase and said enzyme interreactive with the product of the reaction of said lipase with the analyte is glycerol dehydrogenase.

15. The composition of claim 13 wherein said analyte-specific enzyme is hexokinase and said enzyme interreactive with the product of the reaction of said hexokinase with the analyte is glucose-6-phosphate dehydrogenase.

16. The composition of claim 1 wherein said interreactive component is a substrate of the analyte.

17. The composition of claim 16 wherein said interreactive component is a reduced substrate.

18. The composition of claim 17 wherein said interreactive component is lactate.

19. The composition of claim 17 wherein said interreactive component is β-hydroxybutyric acid.

20. The composition of claim 17 wherein said interreactive component is α-hydroxybutyric acid.

21. The composition of claim 17 wherein said interreactive component is ethanol.

22. The composition of claim 17 wherein said interreactive component is a steroid.

23. The composition of claim 22 wherein said interreactive component is cholesterol.

24. The composition of claim 17 wherein said interreactive component is glucose.

25. The composition of claim 1 wherein said at least one interreactive constituent is an analyte-specific substrate and an enzyme interreactive with the product of the reaction of said analyte-specific substrate with the analyte.

26. The composition of claim 25 wherein said analyte-specific substrate is a triglyceride and said enzyme interreactive with the product of the reaction of said triglyceride with the analyte is glycerol dehydrogenase.

27. The composition of claim 25 wherein said analyte-specific substrate is glucose and said enzyme interreactive with the product of the reaction of said glucose with the analyte is glucose-6-phosphate dehydrogenase.

28. The composition of claim 1 wherein said hydroxylase capable of being uncoupled is salicylate hydroxylase and said pseudosubstrate is a benzoate.

29. The composition of claim 1 wherein said hydroxylase capable of being uncoupled is p-hydroxybenzoate hydroxylase and said pseudosubstrate is 6-hydroxynicotinate.

30. The composition of claim 1 wherein said peroxidatively active substance is a peroxidase.

31. The composition of claim 1 wherein said hydrazone is 3-methyl-2-benzothiazolinone hydrazone.

32. The composition of claim 31 wherein said coupler is primaquine.

33. A device for the determination of an analyte in a sample which comprises a carrier incorporated with the composition of claim 1.

34. A method for the determination of an analyte in a sample which comprises contacting said sample with the device of claim 33 and observing any resultant color change thereon.

35. A process for preparing a device for the determination of an analyte in a sample which comprises incorporating a carrier with the composition of claim 1.

36. A method for the determination of an analyte in a sample which comprises contacting said sample with the composition of claim 1 and observing any resultant color change.

* * * * *

UNITED STATES PATENT AND TRADEMARK OFFICE
CERTIFICATE OF CORRECTION

PATENT NO. : 4,394,444

DATED : July 19, 1983

INVENTOR(S) : E.R.Cameron; C.R.Gunter; R.H.White-Stevens

It is certified that error appears in the above-identified patent and that said Letters Patent are hereby corrected as shown below:

The cover page should include

Related U.S. application data [63] Continuation of U.S. Serial No. 83,408 filed October 10, 1979, now abandoned.

Signed and Sealed this

Seventh Day of August 1984

[SEAL]

Attest:

GERALD J. MOSSINGHOFF

Attesting Officer

Commissioner of Patents and Trademarks